United States Patent
Hammond et al.

(10) Patent No.: US 7,056,351 B2
(45) Date of Patent: Jun. 6, 2006

(54) OXIDATIVE HAIR DYE COMPOSITION CONTAINING POLYAKYLENEGLYCO(N)ALKYLAMINE AND A SOLID FATTY COMPOUND

(75) Inventors: Roger Clive Hammond, Staines (GB); Nicholas William Geary, Blue Ash, OH (US)

(73) Assignee: The Procter & Gamble Company, Cincinnat, OH (US)

(*) Notice: Subject to any disclaimer, the term of this patent is extended or adjusted under 35 U.S.C. 154(b) by 100 days.

(21) Appl. No.: 10/459,867

(22) Filed: Jun. 12, 2003

(65) Prior Publication Data

US 2003/0233714 A1 Dec. 25, 2003

Related U.S. Application Data

(63) Continuation of application No. PCT/US01/48599, filed on Dec. 7, 2001.

(30) Foreign Application Priority Data

| Dec. 13, 2000 | (GB) | 0030369 |
| May 8, 2001 | (GB) | 0111166 |
| Aug. 16, 2001 | (GB) | 0120049 |

(51) Int. Cl.
*A61K 7/13* (2006.01)
(52) U.S. Cl. ........ 8/405; 8/406; 8/408; 8/421; 8/552; 8/580; 8/609
(58) Field of Classification Search ........ 8/405, 8/406, 408, 421, 552, 554, 580
See application file for complete search history.

(56) References Cited

U.S. PATENT DOCUMENTS

| 4,563,347 A | 1/1986 | Starch ........ 424/70 |
| 4,698,065 A | 10/1987 | Hoeffkes et al. ........ 8/409 |
| 4,874,604 A | 10/1989 | Sramek ........ 424/171 |
| 5,078,748 A | 1/1992 | Akram et al. ........ 8/405 |
| 5,114,428 A | 5/1992 | Hoeffkes ........ 8/405 |
| 5,230,710 A | 7/1993 | Akram ........ 8/408 |
| 5,376,146 A * | 12/1994 | Casperson et al. ........ 8/408 |
| 5,613,985 A | 3/1997 | Bauer ........ 8/409 |
| 5,747,435 A | 5/1998 | Patel ........ 510/119 |
| 5,756,436 A | 5/1998 | Royce ........ 510/22 |
| 5,804,171 A | 9/1998 | Audousset ........ 424/704 |
| 6,660,045 B1 * | 12/2003 | Hoeffkes et al. ........ 8/405 |

FOREIGN PATENT DOCUMENTS

| EP | 0275707 B1 | 5/1992 |
| GB | 2186889 A | 8/1987 |
| JP | 09040533 A | 10/1997 |
| JP | 2899720 B2 | 6/1999 |
| WO | WO-99/29285 | 6/1999 |
| WO | WO 99/29285 * | 6/1999 |
| WO | WO-99/49836 A1 | 10/1999 |
| WO | WO-99/62467 A1 | 12/1999 |
| WO | WO-00/07550 A1 | 2/2000 |
| WO | WO-02/47632 A2 | 6/2002 |
| WO | WO-02/076412 A2 | 10/2002 |

* cited by examiner

*Primary Examiner*—Eisa Elhilo
(74) *Attorney, Agent, or Firm*—Michael J. Sambrook; Brian M. Bolam; Tara M. Rosnell

(57) ABSTRACT

Disclosed are oxidative hair dye compositions containing polyalkyleneglycol(n)alkylamine and a solid fatty compound. One embodiment of the present invention is, for example, an oxidative hair dye composition comprising a first component and a second component wherein said first component comprises at least one oxidative dye or mixture thereof, a polyalkyleneglycol(n)alkylamine of the formula (I):

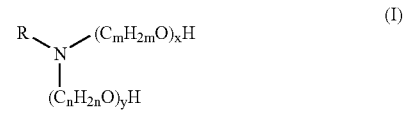

wherein each R is independently a saturated, unsaturated, straight or branched alkyl group having from 1 to about 30 carbon atoms, each m is 2 or 3, each n is 2 or 3, each x and each y are independently a number of 1 or more wherein the sum of each x and each y is from about 2 to about 9; and wherein the melting point of the polyalkyleneglycol(n) alkylamine is less than about 55° C.; a solid fatty compound; and water and wherein said second component comprises at least one oxidising agent and wherein the viscosity of said first and said second component are independently from greater than 1.0 Pas to 20 Pas.

14 Claims, No Drawings

OXIDATIVE HAIR DYE COMPOSITION CONTAINING POLYAKYLENEGLYCO(N)ALKYLAMINE AND A SOLID FATTY COMPOUND

CROSS REFERENCE TO RELATED APPLICATION

The application is a continuation of International application PCT/US01/48599 filed on Dec. 7, 2001.

FIELD OF THE INVENTION

The present invention relates to an oxidative hair dye composition containing polyalkyleneglycol(n)alkylamine and a solid fatty compound.

BACKGROUND OF THE INVENTION

The alteration of the colour of hair by the application of hair dyes is well known. In order to provide the consumer with the hair colour and intensity of shade desired, a very complex chemical process is utilised. The hair dyeing molecules are typically produced from the reaction of at least one oxidative dyeing agent with an oxidising agent, which are formed in situ on the hair of consumers and typically in an aggressive environment at ca pH 10 and in the presence of alkalising agent. Moreover this process is repeated regularly by the consumer in order maintain the desired hair colour and intensity of the hair colour shade and ensure continual, even coverage of the hair including coverage of new hair growth.

These oxidative dyeing systems are typically supplied to the consumer as two separate components one comprising the oxidising agent and the other comprising the oxidative dyeing agent. The consumer is then required to mix these two components prior to application to the hair. In order to facilitate the easy application of the resultant mixture on the hair it is necessary that the applied composition has a certain viscosity. This can be achieved by either supplying each component such that they have the desired viscosity prior to mixing and this viscosity is maintained after mixing. These formulations are typically provided as a cream and are referred to as a thick, thick, thick systems. Alternatively, the two components may be provided as relatively thin fluids which contain materials which on mixing cause the viscosity of the resultant mixture to rapidly increase to the desired level. These systems are referred to as a thin, thin, thick systems and are typically gel type compositions. Such thin compositions are described in U.S. Pat. No. 4,698,065 and WO99/29285.

The manufacturer of oxidative hair dye compositions is also required to work within a large number of constraints. Since these products are being placed in direct contact with the consumers' skin and potentially accidental contact with the eye or ingestion (for example) can occur during the dyeing process, the formulation must meet rigorous safety requirements and not cause any allergic reaction. In addition to meeting these requirements, the products must also be optically and olfactory pleasing to the consumer and meet certain physical parameters in order to ensure that the product can be easily applied to the hair by the consumer to provide the desired effect, without unintentional staining on the consumers clothes, skin or other objects.

The chemistry involved in the hair dyeing process may result in some damage to the hair which is permanent. Damaging effects include tangling, brittleness and dryness. Consequently there is a need to provide the hair dye composition or hair dyeing kit with a conditioning component in order to combat this damage and improve at least the consumers' perception of the condition of the hair; immediately after the hair dyeing process and the on-going condition of the hair during the post dyeing washing cycle until the next hair dyeing cycle.

The use of conditioning compositions is well known in the art and is incorporated as part of conventional shampoo and conditioning regimes as well as in so called two-in-one shampoo conditioners. Their use in hair dyeing kits is also well known. Typically they are provided in a sachet for use in the final rinse, after dyeing is completed. These conditioners such as amino silicones as described for example in U.S. Pat. No. 4,563,347, EP 275 707 and WO99/49836 usually provide an acceptable immediate improved feel of the hair to the consumer. Although, this conditioning benefit offers some durability over a number of hair washing cycles; the consumers still become dissatisfied with the condition of the hair during the course of the post dyeing cycle. Moreover silicone materials are expensive and are difficult to incorporate into formulations without causing stability problems.

Unfortunately durable conditioning cannot be achieved by simply increasing the levels of conditioning material in the composition. In fact, if excessive amino-silicone based conditioner is applied, the initial feel of the hair becomes heavy and greasy which is completely unacceptable to the consumer.

Moreover if the conditioning material is such that it is sustained on the hair during the post dyeing wash cycle and is still present on the hair at the start of the next dyeing cycle, the performance of the dyeing process cannot be predicted and may be detrimentally affected. Such a result is equally undesirable for the consumer.

However, there is still a significant need to provide durable conditioning materials for use in oxidative hair dye compositions which have the required initial deposition and retention over time without any greasy feel negatives after the initial application and which do not negatively affect the performance of the next hair dyeing cycle.

There is also a need to provide a hair dye composition, which does not necessarily require a separate post hair dyeing conditioning step.

There is a further need to provide a hair dye composition, which is easy to formulate and does not cause any stability problems.

SUMMARY OF THE INVENTION

The present invention relates to an oxidative hair dye composition comprising at least one oxidative dye and at least one oxidising agent in separate components and a first component and a second component, said first component comprising (a) polyalkyleneglycol(n)alkylamine of the formula (I):

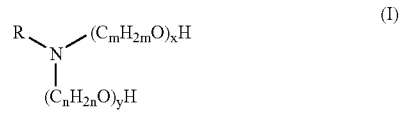

wherein each R is independently a saturated, unsaturated, straight or branched alkyl group having from 1 to about 30 carbon atoms, each m is 2 or 3, each n is 2 or 3, each x and each y are independently a number of 1 or more wherein the sum of each x and each y is from about 2 to about 9; and wherein the melting point of the polyalkyleneglycol(n)alkylamine is less than about 55° C.;

(b) solid fatty compound and
(c) water and and wherein the viscosity of said first and said second components are independently from greater than 1.0 Pas to 20 Pas as measured at 20° C., by means of a Brookfield Viscometer at shear rate of 4.0 rpm with a S41 spindle.

Whilst not being bound by theory it is believed that the essential components of the compositions of the present invention result in an unexpected synergic conditioning effect. This is believed to be due to the two characteristics of the components of the present invention. Firstly the selection of the combination of the essential components themselves, specifically the narrow range of pegylation of the polyalkyleneglycol(n)alkylamine provides improved conditioning. Secondly these essential components also result in the formation of microscopic lamellar structures. These lamellar structures increase the viscosity of the composition, which further provide an improved conditioning benefit verses compositions which have low viscosity, i.e. a thin, thin, thick system.

Polyalkyleneglycol(n)alkylamine and polyalkyleneglycol (n)alkylammonium salts have been previously used in some marketed products. Specifically, Marketed products L'Oreal Feria and Recital contain PEG-2-Tallowamine and or PEG-2-Olealamine. These marketed products however are both Thin-Thin-Thick systems and hence will not have the required viscosity and hence not provide the conditioning benefit as described hereinafter.

DETAILED DESCRIPTION OF THE INVENTION

All percentages, ratios and proportions herein are by weight of the final hair care composition, unless otherwise specified. All molecular weights herein are weight average molecular weights, unless otherwise specified. All temperatures are in degrees Celsius (° C.) unless otherwise specified.

As used herein, the term "alkyl" means a hydrocarbyl moiety which is straight, branched, or cyclic, saturated or unsaturated. Unless otherwise specified, alkyl moieties are preferably saturated or unsaturated with double bonds, preferably with one or two double bonds. Included in the term "alkyl" is the alkyl portion of acyl groups.

As used herein, the term "water-insoluble" means the compound is substantially not soluble in water at 25° C., when the compound is mixed with water at a concentration by weight of above 1.0%, preferably at above 0.5%, the compound is temporarily dispersed to form an unstable colloid in water, then is quickly separated from water into two phases.

Oxidative Hair Dyeing Agents

The concentration of each oxidative hair dyeing agent in the dyeing compositions according to the present invention is preferably from about 0.0001% to about 5% by weight. The exact amount is dependant upon the end shade required. Typically blond shades comprise from 0.0001% to 1.00%, red shades comprise 0.0010% to 4%, brown shades comprise 0.0100% to 4.00% and black shades comprise 0.100 to 4.00% by weight of the total composition on the hair.

Any oxidative hair dyeing agent can be used in the compositions herein. Typically, but without intending to be limited thereby, oxidative hair dyeing agents, consist essentially of at least two components, which are collectively referred to as dye forming intermediates (or precursors). Dye forming intermediates can react in the presence of a suitable oxidant to form a coloured molecule.

The dye forming intermediates used in oxidative hair colorants include: aromatic diamines, aminophenols, various heterocycles, phenols, napthols and their various derivatives. These dye forming intermediates can be broadly classified as; primary intermediates and secondary intermediates. Primary intermediates, which are also known as oxidative dye precursors, are chemical compounds which become activated upon oxidation and can then react with each other and/or with couplers to form coloured dye complexes. The secondary intermediates, also known as colour modifiers or couplers, are generally colourless molecules which can form colours in the presence of activated precursors/primary intermediates, and are used with other intermediates to generate specific colour effects or to stabilise the colour.

Primary intermediates suitable for use in the compositions and processes herein include: aromatic diamines, polyhydric phenols, amino phenols and derivatives of these aromatic compounds (e.g., N-substituted derivatives of the amines, and ethers of the phenols). Such primary intermediates are generally colourless molecules prior to oxidation.

While not wishing to be bound by any particular theory it is proposed herein that the process by which colour is generated from these primary intermediates and secondary coupler compounds generally includes a stepwise sequence whereby the primary intermediate can become activated (by oxidation), and then enjoins with a coupler to give a dimeric, conjugated coloured species, which in turn can enjoin with another 'activated' primary intermediate to produce a trimeric conjugated coloured molecule.

Oxidative Dye Precursors

In general terms, oxidative dye primary intermediates include those monomeric materials which, on oxidation, form oligomers or polymers having extended conjugated systems of electrons in their molecular structure. Because of the new electronic structure, the resultant oligomers and polymers exhibit a shift in their electronic spectra to the visible range and appear coloured. For example, oxidative primary intermediates capable of forming coloured polymers include materials such as aniline, which has a single functional group and which, on oxidation, forms a series of conjugated imines and quinoid dimers, trimers, etc. ranging in colour from green to black. Compounds such as p-phenylenediamine, which has two functional groups, are capable of oxidative polymerization to yield higher molecular weight coloured materials having extended conjugated electron systems. Oxidative dyes known in the art can be used in the compositions according to the present invention. A representative list of primary intermediates and secondary couplers suitable for use herein is found in Sagarin, "Cosmetic Science and Technology", "Interscience, Special Ed. Vol. 2 pages 308 to 310. It is to be understood that the primary intermediates detailed below are only by way of example and are not intended to limit the compositions and processes herein.

The primary intermediates can be used herein alone or in combination with other primary intermediates, and one or more can be used in combination with one or more couplers. The choice of primary intermediates and couplers will be determined by the colour, shade and intensity of coloration which is desired. The primary intermediates and couplers can be used herein, singly or in combination, to provide dyes having a variety of shades ranging from ash blonde to black; these are: pyrogallol, resorcinol, p-toluenediamine, p-phenylenediamine, o-phenylenediamine, m-phenylenediamine, o-aminophenol, p-aminophenol, 4-amino-2-nitrophenol, nitro-p-phenylenediamine, N-phenyl-p-phenylenediamine, m-aminophenol, 2-amino-3-hydroxypyridine, 1-napthol, N,N bis (2-hydroxyethyl)p-phenylenediamine, 4-amino-2-hydroxytoluene, 1,5-dihydroxynapthalene, 2-methyl resorcinol and 2,4-diaminoanisole. These can be used in the molecular form or in the form of peroxide-compatible salts.

For example low intensity colours such as natural blond to light brown hair shades generally comprise from about 0.001% to about 4%. This may be achieved by the combination of primary intermediates such as 1,4-diamino-benzene, 2,5-diamino toluene, 2,5-diamino-anisole, 4-aminophenol, 2,5-diamino-benzyl alcohol and 2-(2',5'-diamino) phenyl-ethanol with couplers such as resorcinol, 2-methyl resorcinol or 4-chloro resorcinol. Similarly combination of the above primary intermediates with couplers, such as, 5-amino-2-methyl phenol and 1,3-diamino-benzene derivatives such as 2,4-diamino-anisole can lead to medium intensity red colours. High intensity colours such as blue to blue-violet hair shades can be produced by the combination of the above primary intermediates with couplers such as 1,3-diamino-benzene or its derivatives such as 2,5-diamino-toluene at levels of from about 1% to about 4% by weight of composition.

Non Oxidative and Other Hair Dyeing Agents

The hair dyeing compositions of the present invention may, in addition to an oxidative hair dyeing agent, include non-oxidative and other dye materials. Optional non-oxidative and other dyes suitable for use in the hair dyeing compositions and processes according to the present invention include both semi-permanent, temporary and other dyes. Non-oxidative dyes as defined herein include the so-called 'direct action dyes', metallic dyes, metal chelate dyes, fibre reactive dyes and other synthetic and natural dyes. Various types of non-oxidative dyes are detailed in: 'Chemical and Physical Behaviour of Human Hair' 3rd Ed. by Clarence Robbins (pp 250–259); 'The Chemistry and Manufacture of Cosmetics'. Volume IV. 2nd Ed. Maison G. De Navarre at chapter 45 by G. S. Kass (pp 841–920); 'cosmetics: Science and Technology' 2nd Ed., Vol. II Balsam Sagarin, Chapter 23 by F. E. Wall (pp 279–343); 'The Science of Hair Care' edited by C. Zviak, Chapter 7 (pp 235–261) and . 'Hair Dyes', J. C. Johnson, Noyes Data Corp., Park Ridge, U.S.A. (1973), (pp 3–91 and 113–139).

Oxidising Agents

The hair dyeing compositions herein comprise at least one oxidising agent, which may be an inorganic or organic oxidising agent. The oxidising agent is preferably present in the dyeing composition at a level of from about 0.01% to about 6%, more preferably from about 1% to about 6% by weight of the composition.

Inorganic Oxidising Agents

A preferred oxidising agent for use herein is an inorganic peroxygen oxidising agent. The inorganic peroxygen oxidising agent should be safe and effective for use in the compositions herein. Preferably, the inorganic peroxygen oxidising agents suitable for use herein will be soluble in the compositions according to the present invention when in liquid form or in the form intended to be used. Preferably, inorganic peroxygen oxidising agents suitable for use herein will be water-soluble. Water soluble oxidising agents as defined herein means agents which have a solubility to the extent of about 10 g in 1000 ml of deionised water at 25° C. ("Chemistry" C. E. Mortimer. 5th Edn. p 277).

The inorganic peroxygen oxidising agents useful herein are generally inorganic peroxygen materials capable of yielding peroxide in an aqueous solution. Inorganic peroxygen oxidising agents are well known in the art and include hydrogen peroxide, inorganic alkali metal peroxides such as sodium periodate, sodium perbromate and sodium peroxide, and inorganic perhydrate salt oxidising compounds, such as the alkali metal salts of perborates, percarbonates, perphosphates, persilicates, persulphates and the like. These inorganic perhydrate salts may be incorporated as monohydrates, tetrahydrates etc. Mixtures of two or more of such inorganic peroxygen oxidising agents can be used if desired. While alkali metal bromates and iodates are suitable for use herein the bromates are preferred. Highly preferred for use in the compositions according to the present invention is hydrogen peroxide.

In preferred dyeing compositions herein the inorganic peroxygen oxidising agent is present at a level of from about 0.01% to less than about 6%, preferably from about 0.01% to about 6%, more preferably from about 1% to about 6%, more preferably from about 3% to about 4.5% by weight of the total composition on hair.

Preformed Organic Peroxy Acid

The compositions herein may instead or in addition to the inorganic peroxygen oxidising agent(s), comprise one or more preformed organic peroxyacid oxidising agents.

Suitable organic peroxyacid oxidising agents for use in the dyeing compositions according to the present invention have the general formula: R—C(O)OOH, wherein R is selected from saturated or unsaturated, substituted or unsubstituted, straight or branched chain, alkyl, aryl or alkaryl groups with from 1 to 14 carbon atoms.

Polyalkleneglycol(n)Alkylamine

The oxidative hair dye composition of the present invention contains a polyalkyleneglycol(n)alkylamine, typically having a melting point of less than about 55° C., more preferably less than about 45° C., most preferably less than 30° C.

Without intending to be limited by theory, it is believed that polyalkyleneglycol(n)alkylamine in the presence of a solid fatty compound can provide an improved matrix, i.e., a higher level of matrix, provides significant consumer desirable benefits, such as an improved condition, look and feel for hair and improved combing both initially and over the colouring cycle.

Without intending to be limited by theory, the matrix is believed to significantly improve deposition of the polyalkyleneglycol(n)alkylamine onto the hair. In a highly preferred embodiment, the matrix is a lamellar cream, which provides improved deposition, wet hair feel, softness, and other substantial benefits. The matrix may become unstable or, at worst, become destroyed in the presence of certain components such as high levels of anionic surfactants, film-forming polymers having anionic moieties and high levels of low molecular weight alcohols. Such low molecular weight alcohols are used in so called thin, thin, thick oxidative dye systems as disclosed in U.S. Pat. No. 4,698,065 and WO99/29285. The present invention differs from such thin, thin, thick systems in that it is important to form this matrix. The matrix improves the conditioning benefit verses other systems which whilst containing polyalkyleneglycol(n)alkylamine do not contain the components required to form the matrix. For example U.S. Pat. No. 4,689,065 and WO99/29285 both describe the use of high levels of water soluble alcohols which would result in compositions which do not comprise a matrix. Moreover these documents describe the desirability of a thin liquid composition i.e. not a cream.

Without further intending to be limited by theory, it is additionally believed that the polyalkyleneglycol(n)alkylamine useful herein provide an initial and durable conditioning benefit by the following mechanism: The amino and hydrophobic alkyl moieties help the compound to attach to hair fibers, even under rinse-off conditions, while the hydrophilic alkoxylate groups attract water molecules and function as a moisture buffer to slow down water content change in the hair fibers. This helps maintain the hair fibers in a flexible, soft, and plastic state. This in turn, allows the hair fiber to maintain a well-aligned conformation (with respect to other hair fibers) and to easily recover from deformation (combing) and hence reducing combing force.

Consistent with the above non-binding theory the number of alkoxy groups are thus deemed important and only a only a specific range (as detailed below) provides the conditioning benefit. The prior art whilst disclosing these materials in general terms neither recognises the importance of degree of alkoxylation nor the restriction of forming specific rheological structures and associated conditioning benefits thereof.

The polyalkyleneglycol(n)alkylamine useful in the present invention has a general formula (I):

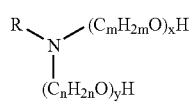

wherein each R is independently a saturated, unsaturated, straight or branched alkyl group having from 1 to about 30 carbon atoms, preferably from about 8 to about 22 carbon atoms, more preferably from about 10 to about 18 carbon atoms; each m is 2 or 3, preferably 2; each n is 2 or 3, preferably 2; each x and each y are independently a number of 1 or more wherein the sum of each x and each y is from about 2 to about 9, preferably from 2 to 5.

Highly preferred polyethyleneglycol(n)alkylamines useful in the present invention are polyethyleneglycol-5-oleylamine, also abbreviated as PEG-5 oleylamine, wherein the sum of x and y is about 5; and polyethyleneglycol-5-cocamine also abbreviated as PEG-5 cocamine, wherein R is substantially made of straight chain alkyls having 10–16 carbon atoms, and the sum of x and y is about 5.

The polyalkyleneglycol(n)alkylamine is preferably present at a level of from about 0.1% to about 5%, more preferably from about 0.25% to about 3%, and still preferably from about 0.5% to about 2%, by weight of the hair care composition.

Particularly preferable and commercially available polyalkyleneglycol(n)alkylamines are; PEG-5-oleylamine (tradename Varonic Q-205), PEG-5-cocamine (tradename Varonic K-205), both available from Th. Goldschmidt AG, PEG-3 Cocamine (tradename C-243) and PEG-2 Soyamine sold as part of a blend under the tradename C-216; the latter two both available from Lowenstein and Son. Additional highly preferred polyalkyleneglycol(n)alkylamines are PEG-2 Rapeseedamine, PEG-5 lauramine, PEG-6 Soyamine, PEG-3-soyamine, PEG-2 oleylamine and PEG8-Stearylamine.

Solid Fatty Compound

The composition of the present invention further comprises as an essential feature a solid fatty compound. The solid fatty compound useful herein has a melting point of 25° C. or higher, and is selected from the group consisting of fatty alcohols, fatty acids, and mixtures thereof. It is understood by the artisan that the compounds disclosed in this section of the specification can in some instances fall into more than one classification, e.g., some fatty alcohol derivatives may also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

The solid fatty compound is preferably included in the composition at a level by weight of from about 0.1% to about 20%, more preferably from about 1% to about 15%, still preferably from about 1% to about 10%.

The fatty alcohols useful herein are those having from about 14 to about 30 carbon atoms, preferably from about 16 to about 22 carbon atoms. These fatty alcohols are saturated and can be straight or branched chain alcohols. Nonlimiting examples of fatty alcohols include, cetyl alcohol, stearyl alcohol, behenyl alcohol, and mixtures thereof.

The fatty acids useful herein are those having from about 10 to about 30 carbon atoms, preferably from about 12 to about 22 carbon atoms, and more preferably from about 16 to about 22 carbon atoms. These fatty acids are saturated and can be straight or branched chain acids. Also included are diacids, triacids, and other multiple acids which meet the requirements herein. Also included herein are salts of these fatty acids. Non-limiting examples of fatty acids include lauric acid, palmitic acid, stearic acid, behenic acid, sebacic acid, and mixtures thereof.

Solid fatty compounds of a single compound of high purity are preferred. Single compounds of pure fatty alcohols selected from the group of pure cetyl alcohol, stearyl alcohol, and behenyl alcohol are highly preferred.

By "pure" herein, what is meant is that the compound has a purity of at least about 90%, preferably at least about 95%. These single compounds of high purity may provide good rinsability from the hair when the consumer rinses off the composition.

Among the solid fatty compounds described above, fatty alcohols are highly preferred in the present invention.

Water

The compositions of the present invention also further comprise water. Deionized water is preferably used. Water from natural sources including mineral cations can also be used, depending on the desired characteristic of the product. Generally, the compositions of the present invention comprise at least about 60%, preferably at least about 70% water, and more preferably from about 75% to about 95% water. Deionized water is preferably used. Water from natural sources including mineral cations may also be used, depending on the desired characteristic of the product.

Viscosity

According to the present invention the first and a second components of the present invention independently have a viscosity of from greater than 1.0 to 20 Pas, preferably from 1.5 to 10 Pas more preferably from 2 to 5 Pas, most preferably from 2 to 3 Pas, as measured at 20° C., by means of a Brookfield Viscometer, spindle S41, at shear rate of 4.0 rpm. Moreover, preferably when the first and second components are mixed together prior to application onto the hair by the consumer the resultant mixture typically has a viscosity of from greater than 1.0 to 20 Pas, preferably from 2 to 5 Pas, more preferably from 2 to 3 Pas.

Additional Components

Certain additional components are preferred in the present invention. Preferred additional components include organic acids, surfactants, conditioning agents, alkyl ethoxylate, hydrocarbons, silicone compounds, cationic polymers, and mixtures thereof. Unless otherwise noted, such additional components generally are typically used individually at levels from about 0.001% to about 10.0%, preferably from about 0.01% to about 5.0% by weight of the composition.

Organic Acid

In a preferred embodiment of the present invention it is believed that the amine moieties of the polyalkyleneglycol (n)alkylamine are positively charged in the presence of an organic acid, which is attracted and deposited on the surface of the hair. Thus, together with the moisturizing effect to the hair fiber, the polyalkyleneglycol(n)alkylamines provide a desirable durable conditioning effect.

The composition of the present invention hence preferably comprises an organic acid. The organic acids useful herein are those having at least one acidic group, their salts, and mixtures thereof. Preferably the organic acid comprises an alkyl chain having from 4 to 22 carbon atoms. Highly preferred organic acid useful herein includes, for example, oleic acid, linolenic acid, linoleic acid, erucic acid, gadoleic acid, stearic acid, palmitic acid, citric acid, aconitic acid, ethylenediaminetetraacetic acid, their salts, and mixtures thereof. Most preferably the organic acid is selected from oleic acid, linolenic acid, linoleic acid and mixtures thereof.

Without intending to be limited by theory, it is believed that the organic acid together with a solid fatty compound, and the polyalkyleneglycol(n)alkylamine can provide an improved gel matrix which may be due to the linkage formed between each acidic group of the organic acid and the polyalkyleneglycol(n)alkylamine.

In the composition of the present invention, the organic acid is preferably included at a level to provide a certain mole ratio, for example, of A (acidic groups from the organic acids) to B (amine groups from polyalkyleneglycol(n)alkylamines), when polyalkyleneglycol(n)alkylamine of the formula (I) is used in the present invention. The mole ratio of A to B is preferably from about 1:5 to about 5:1, more preferably from about 1:2 to about 2:1.

Cationic Polymer

The hair care compositions of the present invention may contain one or more cationic polymers. As used herein, the term "polymer" includes materials whether made by polymerization of one type of monomer or made by two (i.e., copolymers) or more types of monomers. Preferably, the cationic polymer is a water-soluble cationic polymer. As used herein, the term "water soluble" cationic polymer, indicates a polymer which is sufficiently soluble in water to form a substantially clear solution to the naked eye at a concentration of 0.1% in water (distilled or equivalent) at 25° C. The preferred cationic polymer will be sufficiently soluble to form a substantially clear solution at 0.5% concentration, more preferably at 1.0% concentration. If present, the cationic polymer is typically at a level of preferably from about 0.1% to about 5%, more preferably from about 0.5% to about 3% by weight of the composition.

The cationic polymers herein will generally have a weight average molecular weight, which is at least about 5,000, typically from about 10,000 to about 10 million. Preferably, the weight average molecular weight is from about 100,000 to about 2 million. The cationic polymer will generally have cationic nitrogen-containing moieties such as quaternary ammonium or cationic amino moieties, and mixtures thereof.

The cationic nitrogen-containing moiety will be present generally as a substituent, on a fraction of the total monomer units of the cationic hair conditioning polymers. Thus, the cationic polymer may comprise copolymers, terpolymers, etc. of quaternary ammonium or cationic amine-substituted monomer units and other non-cationic units referred to herein as spacer monomer units. Such polymers are known in the art, and a variety may be found in the CTFA Cosmetic Ingredient Dictionary, 3rd edition, edited by Estrin, Crosley, and Haynes, (The Cosmetic, Toiletry, and Fragrance Association, Inc., Washington, D.C., 1982).

Conditioning Agent

In a preferred embodiment of the present invention, the compositions according to the present invention comprise at least one hair conditioning agent. The composition containing cationic surfactants can, together with the essential components, provide an improved matrix which provides still further improved conditioning benefits. The conditioning agent herein can be any conditioning agent suitable for use in conditioning hair.

The conditioning agent is preferably present at a level of from about 0.1% to about 15%, preferably from about 0.5% to about 10%, more preferably from about 1% to about 5%, by weight of the final on head composition.

Suitable conditioning agents for use herein include, but are not limited to, cationic surfactants, insoluble silicones, non-volatile hydrocarbons, non-volatile hydrocarbon esters, and mixtures thereof. Other suitable conditioning agents are disclosed in WO95/20939 and WO96/32919 which are incorporated herein by reference.

Preferred conditioning agents for use herein include cationic surfactants, cationic polymers, insoluble silicone conditioning agents, amino functionalised silicones and saturated C14–C22 straight chain fatty alcohols and mixtures thereof.

When present, the insoluble silicone conditioning agents are present at a level of from about 0.1 to 10%, preferably from about 0.1% to about 5%, more preferably from about 1% to about 3% by weight of composition. Suitable insoluble silicones include polyalkyl siloxanes, polyaryl siloxanes, polyalkylaryl siloxanes, polether siloxane copolymers, and mixtures thereof. The silicone conditioning agent will preferably be non-volatile. As used herein the term "non-volatile" shall mean that the material has a boiling point of at least about 260° C., preferably at least about 275° C., more preferably at least about 300° C. Such materials exhibit very low or no significant vapour pressure at ambient conditions. The term "silicone fluid" shall mean flowable silicone materials having a viscosity of less than 1,000,000 centistokes at 25° C. The term "silicone gum" shall mean flowable silicone materials having a viscosity of 1,000,000 centistokes at 25° C. or greater. The viscosity can be measured by a glass capillary viscometer as in Dow Corning Corporate Test Method CTM0004, Jul. 20, 1920, or equivalent.

A preferred silicone material for use herein is a polydimethyl siloxane. These silicones are available for example from the General Electric Company in their Viscasil and SF96 series, and from Dow Corning in their Dow Corning 200 series.

Other suitable insoluble silicones for use herein are disclosed in WO96/32919, which is incorporated herein by reference.

A particularly preferred silicone conditioning agent for use herein is least one or a mixture of an amino functional polysiloxane compound having the formula:

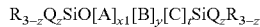

wherein; A represents $R_2SiO$, B represents RQSiO and C represents $R_{3-z}Q_z[A]_{x2}SiOR^1$, wherein R is an alkyl group of 1 to 5 carbons wherein at least 50% of said R groups are methyl, preferably R is a methyl, ethyl, propyl, isopropyl, butyl or isobutyl, a phenyl group, an alkoxy group or an hydroxy group and $R^1$ is R or Q or $R^2$, $R^2$ is $R_{3-z}Q_z[A]_{x3}$ wherein, Q is an amine functional group of the formula —$R^3Z$, $R^3$ is a divalent alkylene radical of 3 to 6 carbons, preferably trimethylene, pentamethylene, —$CH_2CHCH_3CH_2$—, or —$CH_2CH_2CHCH_3CH_2$—, Z is —$N(R^4)_2$, —$NR^4(CH_2)_nN(R^4)_2$, —$N^+(R^4)_3A^-$, $NR^4(CH_2)_n$ $N^+(R^4)_3A^{-'}$ preferably a manovalent radical including at least 1 amine; unsubstituted amine radical —$NH_2$, alkyl substituted amine radicals such as —$NHCH_3$ to —$NHCH_2CH_2CH_3$; aminoalkyl substituted amine radicals such as —$NHCH_2CH_2NH_2$, —$NH(CH_2)_6NH_2$ and —$NHCH_2CH_2N(CH_3)_2$; diaminoalkyl substituted amine radicals such as —$N(CH^2CH_2CH_2NH_2)_2$—N $(CH_2CH_2CH_2N(CH_3)_2)_2$, $R^4$ is an H atom or alkyl group of 1 or 20 carbon atoms or phenyl or benzyl, $A^-$ is $F^-$, $Cl^-$, $Br^-$, $I^-$, and wherein :t is from 0 to 3, $x_1$ is from 1 to 3000, $x_2$ is from 0 to 3000, $x_3$ is from 0 to 3000, $x_1+x_2+x_3$ is from 10 to 3000, y is from 0 to 100, preferably y is 0 when z=1 and preferably y is from 1 to 100 when z=0, z is from 0 to 1, and n is from 2 to 6. More preferably R is a methyl or hydroxy or methoxy group, most preferably methyl and at least 50% of R groups are methyl. $R^1$ is R or Q, most preferably R, Q is an amine functional group of the formula —$R^3Z$, $R^3$ is propyl or isobutyl and Z is $NH_2$ or $NHCH_2CH_2NH_2$ and wherein t is from 0 to 2, most preferably 0, $x_1$ is from 10 to 400, $x_2$ is from 22 to 124, $x_1+x_2$ is from 10 to 400, y is from 0 to 9 when z=1, and y is from 1 to 9 when z=0.

Surfactant Materials

The compositions herein can additionally contain a surfactant system. Suitable surfactants for inclusion in the compositions for use in the invention generally have a lipophilic chain length of from about 8 to about 22 carbon atoms and can be selected from anionic, cationic, nonionic, amphoteric, zwitterionic surfactants and mixtures thereof. Particularly preferred are cationic, nonionic and mixtures thereof. Suitable surfactants for use herein are disclosed in WO98/27945, which is incorporated herein by reference in its entirety.

Highly preferred hydrophilically substituted cationic surfactants for use herein include dialkylamido ethyl hydroxyethylmonium salt, dialkylamidoethyl dimonium salt, dialkyloyl ethyl hydroxyethylmonium salt, dialkyloyl ethyldimonium salt, and mixtures thereof; for example, commercially available under the following tradenames; VARISOFT 110, VARISOFT 222, VARIQUAT K1215 and VARIQUAT 638 from Witco Chemicals (Greenwich, Conn., USA), MACKPRO KLP, MACKPRO WLW, MACKPRO MLP, MACKPRO NSP, MACKPRO NLW, MACKPRO WWP, MACKPRO NLP, MACKPRO SLP from McIntyre, ETHOQUAD 18/25, ETHOQUAD O/12PG, ETHOQUAD C/25, ETHOQUAD S/25, and ETHODUOQUAD from Akzo, DEHYQUAT SP from Henkel (Germany), and ATLAS G265 from ICI Americas (Wilmington, Del., USA).

Salts of primary, secondary, and tertiary fatty amines can be used as cationic surfactants. The alkyl groups of such amines preferably have from about 12 to about 22 carbon atoms, and can be substituted or unsubstituted. Particularly useful are amido substituted tertiary fatty amines. Such amines, useful herein, include stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Also useful are dimethylstearamine, dimethylsoyamine, soyamine, myristylamine, tridecylamine, ethylstearylamine, N-tallowpropane diamine, ethoxylated (with 5 moles of ethylene oxide) stearylamine, dihydroxyethylstearylamine, and arachidylbehenylamine. These amines are typically used in combination with an acid to provide the cationic species. The preferred acid useful herein includes L-glutamic acid, lactic acid, hydrochloric acid, malic acid, succinic acid, acetic acid, fumaric acid, tartaric acid, L-glutamic hydrochloride, L-aspartic acid, oleic acid linoleic acid linolenic acid and mixtures thereof.

For preferred methods herein, it is preferable that the hair conditioning and colouring composition comprises less than about 20% surfactant, preferably less than about 10% surfactant. It is also preferable that the hair colour altering compositions comprise less than about 5% anionic surfactant.

Other Additional Components

The compositions of the present invention typically further comprise a number of other components commonly utilised in hair care compositions such as shampoos, conditioners, styling aids and colourants which are well known to those skilled in the art such as for example thickeners and diluents. Additionally a number of optional materials can be added to the compositions herein described each at a level of from about 0.001% to about 5%, preferably from about 0.01% to about 3%, more preferably from about 0.05% to about 2% by weight of composition. Such materials include proteins and polypeptides and derivatives thereof; water-soluble or solubilizable preservatives such as DMDM Hydantoin, Germall 115, methyl, ethyl, propyl and butyl esters of hydroxybenzoic acid, EDTA, Euxyl (RTM) K400, natural preservatives such as benzyl alcohol, potassium sorbate and bisabalol, benzoic acid, sodium benzoate and 2-phenoxyethanol; antioxidants such as sodium sulphite, hydroquinone, sodium bisulphite, sodium metabisulphite and thyoglycolic acid, sodium dithionite, erythrobic acid and other mercaptans; dye removers such as oxalic acid, sulphated castor oil, salicylic acid and sodium thiosulphate; $H_2O_2$ stabilisers such as tin compounds such as sodium stannate, stannic hydroxide and stannous octoate, acetanilide, phenacetin colloidal silica such as magnesium silicate, oxyquinoline sulphate, sodium phosphate, and tetrasodium pyrophosphate; and ρ-hydroxybenzoates; moisturising agents such as hyaluronic acid, chitin, and starch-grafted sodium polyacrylates such as Sanwet (RTM) IM-1000, IM-1500 and IM-2500 available from Celanese Superabsorbent Materials, Portsmith, Va., USA and described in U.S. Pat. No. 4,076,663 as well as methyl cellulose, starch, higher fatty alcohols, paraffin oils, fatty acids and the like; solvents; anti-bacterial agents such as Oxeco (phenoxy isopropanol); low temperature phase modifiers such as ammonium ion sources (e.g. $NH_4Cl$); viscosity control agents such as magnesium sulfate and other electrolytes; quaternary amine compounds such as distearyl-, dilauryl-, di-hydrogenated beef tallow-, dimethyl ammonium chloride, dicetyldiethyl ammoniumethylsulphate, ditallowdimethyl ammonium methylsulphate, disoya dimethyl ammonium chloride and dicoco dimethyl ammonium chloride; enzyme stabilisers such as water soluble sources of calcium or borate species; $TiO_2$ and $TiO_2$-coated mica; perfumes and perfume solubilizers; and zeolites such as Valfour BV400 and derivatives thereof and metal ion sequestrants such as polycarboxylates, amino polycarboxylates, polyphosphonates, amino polyphosphonates etc. and water softening agents such as sodium citrate, inorganic peroxygen oxidsing agents and enzymes. The dyeing compositions used in the methods of the present invention can be formulated over a wide pH range, e.g. from about 2 to about 13, but the compositions are formulated at high pH, preferably in a pH range of from about 8 to about 12, more preferably from about 9 to about 11, most preferably from about 9.5 to 10.5.

The compositions may contain one or more optional buffering agents and/or hair swelling agents (HSAs). Several different pH modifiers can be used to adjust the pH of the final composition or any constituent part thereof. However, preferred compositions herein are substantially free of additional buffering agents, and hair swelling agents, i.e. they comprise less than about 1%, preferably less than about 0.5%, more preferably less than about 0.1% by weight of such agents.

In oxidative dyeing kits comprising a portion of inorganic peroxygen oxidising agent, such as hydrogen peroxide, which may be present in either solid or liquid form, a buffering agent solution can be used to stabilise hydrogen peroxide. Since hydrogen peroxide is stable in the pH range from 2 to 5, it is preferable to use a buffering agent having a pH within this range. Dilute acids are suitable hydrogen peroxide buffering agents.

According to the present invention the oxidative hair dye composition is provided as two separate components. The first component preferably comprises the polyalkyleneglycol alkylamine, the solid fatty compounds and the oxidative dye or dye mixture and the second component typically comprises the oxidising agent. These two components are then mixed by the consumer prior to application to the hair.

EXAMPLES

The following examples further describe and demonstrate the preferred embodiments within the scope of the present invention.

Treatment of Switches with Hair Care Compositions

Hair Switches

The hair switches utilised in the following test are:

Virgin light brown hair 4 g×8" Hair.

Water Settings

The water settings utilised for the following tests are:

Tap water, hardness 8–10 gpg.

Water flow rate 6±0.5 L/min.

Water Temperature 37±2° C.

Sample Preparation

In order to assess the performance of the present invention on hair, which is regularly coloured, the hair switch samples utilised in the test are firstly treated with a market product hair colourant (namely L'Oreal, Excellence No. 01) according to the manufacturers' instructions. Following this treatment the samples are then washed as described below 4 times.
1. Wet switch for 10 seconds.
2. Apply 0.4 ml of Prell shampoo on the hair switch, using a syringe.
3. Lather for 30 seconds using milking action, distributing shampoo on both sides of hair switch.
4. Rinse for 30 seconds.
5. Repeat steps 2, 3 and 4 once.
6. Hot air dry, brushing with a vent brush, whilst blow drying on a high heat/high speed for a total of 3 minutes (1 minute on each side and 1 minute with brushing).

Colouring Composition 9.0% Peroxide Base was mixed 1:1 with the Colourant Conditioning Base and then applied as follows.

Initial Treatment of Sample

The switch is hung above a sink and wetted for 30 seconds with water. Excess water is squeezed out of the switch. 8.0 grams of the colouring composition to be tested is applied on the top end of the switch and spread evenly down to the bottom end, then milked into the switch. The switch is wrapped and the colouring composition is then left on the switch for 30 minutes at 30° C. The switch is then rinsed with water. Excess water is squeezed out of the switch. The initial average combing index value and the initial average sensory index value are calculated by carrying out the combing test and the sensory test described herein on the wet switches.

Final Treatment of Sample

The switches are then washed as described 18 times.
1. Wet switch for 10 seconds.
2. Apply 0.4 ml of Prell shampoo on the hair switch, using a syringe.
3. Lather for 30 seconds using milking action, distributing shampoo on both sides of hair switch.
4. Rinse for 30 seconds.
5. Repeat steps 2,3 and 4 once.
6. Hot air dry, brushing with a vent brush, whilst blow drying on a high heat/high speed for a total of 3 minutes (1 minute on each side and 1 minute with brushing).
7. The final sensory values are determined by carrying out the tests as described herein.

Sensory Evaluation and Descriptive Analysis Panels

Sensory evaluation is designed to measure, analyze & interpret reactions to product characteristics as perceived by the senses of sight, smell, taste, touch and hearing. A commonly used sensory evaluation technique is descriptive analysis. Descriptive analysis is a complete, detailed and objective characterization of the sensory properties of a product using screened and qualified panelists that are specifically trained for this purpose. Descriptive analysis provides information about the perceived sensory properties (or attributes) and the strength of each sensory attribute in quantitative terms. Panelists are trained to rate the intensity of a large number of sensory properties, while ignoring personal preferences. Each sensory attribute is meticulously defined, and panelists are presented with reference materials that represent high, medium and low intensities of each sensory attribute. Panelists work in isolation in a sensory booth, and assess all sensory characteristics of one sample before moving to the next sample. Care is taken to blind and randomize the samples, and to control the environment (lighting, temperature, humidity).

A descriptive analysis panel requires 10 panelists, because the high level of training ensures a low level of variability in the data (small standard deviations). Panelists only qualify when their ratings are consistent from test-to-test, when their ratings are consistent with that of the panel, and when they are sensitive enough to discriminate small differences. Performance of descriptive analysis panels and individual panelists is monitored closely. Typically, each product is evaluated by all panelists once or twice, and the mean attribute ratings across the panelists or panelist means is calculated. Because the intensity scores are recorded in relation to a universal scale, the relative intensities among attributes and among products can be compared. Descriptive analysis ratings are used for quality control & shelf life studies, for product development, and for claim substantiation. The ASTM Guideline E 1958–98 'Standard Guide for Sensory Claim Substantiation" states that descriptive analysis data are suitable for claim substantiation if the panel shows good consistency and robustness, and when the relationship between descriptive sensory attributes and consumer responses is established.

Descriptive Analysis Panel

External Descriptive Analysis Panel at Product Perceptions

A panel consisting of 10 trained females, was used to conduct the tests.

Ease of Detangling:

Technique: With the wide end of the comb, comb 3 times to remove tangles. Assess the difficulty of removing tangles from the sample hair. If longer is needed to remove all the tangles, continue to comb with wide end until all tangles are removed.

Definition: Hard to detangle=The time and force required remove all tangles from the sample hair with the wide end of a comb, from very easy (one stroke) represented by high numbers and a lot of force represented by low numbers.

Not Coarse:

Technique: Assess the coarse or rough feel of the hair by rubbing across the switch with thumb, index and middle fingers in a horizontal direction before and after combing the switches.

Definition: Not Coarse=The absence of coarse or rough feel on the hair, no apparent roughness=100 to very rough=0.

Resistance to Milking

Technique: Assess the resistance encountered when moving the fingers down the length of the switch using a milking motion (1 stroke/second) prior to combing.

Definition: Resistance to Milking=the degree of resistance encountered, from very resistant (not slippery)=0, to not resistant (very slippery)=100.

Example Compositions

The colouring composition was made up before each application by mixing the peroxide cream with the dye cream. The dye cream and the peroxide cream compositions are prepared as described herein after.

Examples of Final Dye Cream Formulations

The following dye cream formulations are to be mixed 1:1 with the peroxide cream.

|  | % in use |
| --- | --- |
| Dye Cream Formula for Dark Shades | |
| Water | QS to 50 |
| Emulsion Base | 24.7500 |
| Dye premix | 14.0000 |
| Decyl glucoside (optional) | 0.5000 |
| 30% Aqueous Ammonium hydroxide | 4.1300 |
| Dye Cream Formula for Reds and Browns | |
| Water | QS to 50 |
| Emulsion Base | 24.7500 |
| Dye premix | 14.0000 |
| Decyl glucoside (optional) | 0.5000 |
| 30% Aqueous Ammonium hydroxide | 5.1000 |
| Dye Cream Formula for Blondes | |
| Water | QS to 50 |
| Emulsion Base | 24.7500 |
| Dye premix | 14.0000 |
| Decyl glucoside (optional) | 0.5000 |
| 30% Aqueous Ammonium hydroxide | 6.0000 |

Examples of Dye Emulsion Base Formulations

The following are examples of the emulsion base premix formulation

Weight Percents are given as % in use

| Emulsion Base Formula | 1 | 2 | 3 | 4 | 5 | 6 |
| --- | --- | --- | --- | --- | --- | --- |
| Water | QS to 24.75% | | | | | |
| Ceteareth-25 | 0.54 | 0.54 | 0.54 | 0.54 | 0.54 | 0.75 |
| Stearyl Alcohol | 1.63 | 1.63 | 1.63 | 1.63 | 1.63 | 1.125 |
| Cetyl Alcohol | 0.81 | 0.81 | 0.81 | 0.81 | 0.81 | 1.125 |
| Benzyl Alcohol | 0.0745 | 0.0745 | 0.0745 | 0.0745 | 0.0745 | 0.0745 |
| Phenoxy-ethanol | 0.0745 | 0.0745 | 0.0745 | 0.0745 | 0.0745 | 0.0745 |
| Steareth-2 | 0.27 | 0.27 | 0.27 | 0.27 | 0 | 0 |
| Tetrasodium EDTA | 0.021 | 0.021 | 0.021 | 0.021 | 0.021 | 0.021 |
| Di-2-PEG Soyamine IPDI | 0.235 | 0.235 | 0 | 0 | 0 | 0 |
| Dow Silicone Q2-8220 | 0 | 1.50 | 0 | 0 | 0 | 0 |
| Dow Silicone Q2-8566 | 0 | 0 | 1.5 | 1.5 | 1.5 | 0 |
| Oleic Acid | 0.825 | 0.825 | 1 | 1 | 0 | 0 |
| PEG-2 Soyamine | 1.175 | 1.175 | 1 | 0 | 2 | 0 |
| PEG-3 Cocamine | 0 | 0 | 0 | 0.895 | 0 | 0 |

Dye Cream Emulsion Making Methods

The Dye Base Emulsions described and exemplified hereinabove can be manufactured utilising any one of the standard approaches, these include:

Oil in water process

Phase Inversion process

One-pot process

The amount of shear should be controlled to allow the desired particle size to be achieved which can be determined utilising the test method described herein.

An example Dye Base Emulsion making method is given below.

One-Pot Process for Making Dye Cream Emulsion

1. Add water to vessel. Heat to above the melt temperature of the fatty alcohols with agitation. Add Fatty Acids, Fatty Alcohols and any Ethoxylated materials, e.g. Ceteareth-25, Cetyl, Stearyl and Steareth-2, Di-2-PEG Soyamine IPDI and allow to melt. Increase agitation.
2. Add other surfactants such as Peg-3 Cocamine, PEG-5 Cocamine and PEG-2 Soyamine.
3. Continue mixing with shear.
4. Begin cooling with shear adding preservatives at appropriate temperature.
5. If silicone conditioning agents are used these are added during cooling with mixing. Mix until homogeneous and desired particle size achieved.
6. Cool to room temperature.

Final Dye Cream Making Method

Below is an example of how the final dye cream can be manufactured:

To the dye cream emulsion add the following:

Decyl glucoside (if used) then mix to give a homogenous product

Dye premix containing: water, anti-oxidants, solvents, precursors and couplers, then mix to give a homogenous product Ammonium hydroxide, then mix to give a homogenous final product Dye Premix Formulations:

The following is a list of typical couplers and precursors used to formulate various shade ranges.

--- p-Phenylenediamine
p-Aminophenol
N4,N4-bis Hydroxyethyl-p-PD sulphate
o-Aminophenol
p-Methylaminophenol
2,5,Diamonotoluene Sulphate
m-Aminophenol
4-amino-2-hydroxytoluene
Resorcinol
2-methyl resorcinol
2-Amino-3-Hydroxypyridine
2-Amino-4-Hydroxyethylaminoanisole sulphate
2-methyl-5-hydroxyethylaminophenol
m-Phenylenediamine.sulphate
1-phenyle-3-methyl-5-pyrazolone
Naphthol

---

Additionally the dye premix formulations may comprise the following additional materials:

---

Water
Reducing Agents such as Sodium Sulphite
Anti-oxidants such as D and L-Ascorbic Acid
Metal Chelants such as EDTA
Relatively low levels of solvents such as glycols

---

Examples of Total Dye Levels used in Various Shades

| Shade | % w/w in use |
|---|---|
| Blondes | 0.0001 to 4.0000 |
| Reds | 0.0010 to 4.0000 |
| Browns | 0.0100 to 4.0000 |
| Blacks | 0.1000 to 5.0000 |

Dye Premix Making Method

The dye premix may be manufactured by simple mixing. An example of a dye premix manufacturing method is as follows:

With mixing add the following:
1. Water, solvents, anti-oxidants, precursors and couplers
2. If required warm to solubilize
3. Cool to room temperature Hydrogen Peroxide Cream Making Method 6% Hydrogen Peroxide Cream

| | % w/w in use |
|---|---|
| Water | QS to 50 |
| Hydrogen Peroxide Emulsion Base | 18.00 |
| Chelator Premix | 7.5 |
| 35% Hydrogen Peroxide | 8.85 |
| pH Adjustment Gap | To pH 1–5 |

Example Making Method for 6% Hydrogen Peroxide Cream

To the Hydrogen Peroxide Emulsion Base add the following with agitation: Water, Chelant Premix and 35% Hydrogen Peroxide Solution, mix until homogeneous. Adjust pH to between one and five with appropriate amounts of phosphoric acid and/or sodium hydroxide 9% Hydrogen Peroxide Cream

| | % w/w in use |
|---|---|
| Water | QS to 50 |
| Hydrogen Peroxide Emulsion Base | 18.00 |
| Chelator Premix | 7.50 |
| 35% Hydrogen Peroxide | 13.3 |
| pH Adjustment Gap | To pH 1–5 |

Example Making Method for 9% Hydrogen Peroxide Cream

To the Hydrogen Peroxide Emulsion Base add the following with agitation: Water, Chelant Premix and 35% Hydrogen Peroxide Solution, mix until homogeneous. Adjust pH to between one and five with appropriate amounts of phosphoric acid and/or sodium hydroxide.

Example of an Hydrogen Peroxide Emulsion Base

| Hydrogen Peroxide Emulsion Base Formula | % w/w in Use (on head) |
| --- | --- |
| Purified Water | QS to 18 |
| Ceteareth-25 | 0.75 |
| Cetyl Alcohol | 1.125 |
| Stearyl Alcohol | 1.125 |

Hydrogen Peroxide Emulsion Base Method

An example of a Hydrogen Peroxide Emulsion Base making method is given below.

One-Pot Process for Making Hydrogen Peroxide Emulsion Base

1. Add water to vessel. With agitation heat to above the melt temperature of the fatty alcohols
2. Add Fatty Alcohols and any Ethoxylated Fatty Alcohols and allow to melt. Increase agitation.
3. Continue mixing with shear until emulsion has formed
4. Begin cooling stopping shear at appropriate temperature.
5. Cool to room temperature Chelator Premix to Stabilise Peroxide

| | % w/w in Formula |
| --- | --- |
| Purified Water | QS to 7.5000 |
| Metal Chelators | 0.0010 to 1.0000% |
| Phosphoric Acid and/or Sodium Hydroxide | Adjust to pH 1–5 |

Example Making Method for Chelant Premix

1. Dissolve the chelants in the water phase

Adjust pH with phosphoric acid and/or sodium hydroxide as required

Data

Viscosity Data (reading in Pas at 1 min and 2 minute data in brackets)

The following Viscosity data were obtained, for which 6% Peroxide Cream was used, except for the competitive products for which the supplied peroxide was used.

| Dye Cream using Emulsion base: | 2 | 3 | L'Oreal Feria | L'Oreal Recital |
| --- | --- | --- | --- | --- |
| Viscosity of Dye Cream (or solution—competitive product) | 2.4 (1.9) | 20.0 (20.0) | 0.05 (0.05) | 0.04 (0.04) |
| Viscosity of Peroxide Cream (or solution—competitive product) | 2.3 (2.2) | 2.3 (2.2) | 0.47 (0.44) | 0.57 (0.63) |
| Combined—in use rheology (50:50 mix or as described in competitive usage instructions) | 2.7 (2.5) | 11.5 (10.0) | 2.6 (2.9) | 1.5 (2.0) |

These results demonstrate that use of the preferred polyalkyleneglycol(n)alkylamine in combination with other essential elements of the present invention yield the preferred highly viscous matrix containing formulation. The competitive examples have significantly lower viscosity.

Sensory Data

Results indexed against Control (Base 6)

| Descriptive Analysis | Base 1 | Base 2 | Base 3 | Base 4 | Base 5 | Base 6 |
| --- | --- | --- | --- | --- | --- | --- |
| Dry Switches | | | | | | |
| Not Coarse | 1.08 | 1.10 | 1.04 | 1.07 | 1.01 | 1.00 |
| Re-Wetted Switches | | | | | | |
| Pre-Comb Resistant to Milking | 1.18 | 1.21 | 1.23 | 1.25 | 1.04 | 1.00 |
| Ease to Detangle | 1.35 | 1.12 | 1.10 | 1.18 | 1.06 | 1.00 |
| Post Comb Not Coarse | 1.14 | 1.00 | 0.94 | 1.03 | 0.97 | 1.00 |
| Wet After Shampoo Rinse | | | | | | |
| Pre-Comb Resistant to Milking | 1.05 | 1.15 | 1.20 | 1.22 | 1.25 | 1.00 |
| Pre-Comb Not Coarse | 1.04 | 1.04 | 1.12 | 1.20 | 0.98 | 1.00 |
| Ease to Detangle | 1.14 | 1.06 | 1.08 | 1.16 | 1.06 | 1.00 |

The sensory data results demonstrate that use of preferred polyalkyleneglycol(n)alkylamine (base 1) of the present invention versus control not containing polyalkyleneglycol(n)alkylamine (base 6) yields improved conditioning for all consumer relevant evaluation conditions. Further, other examples (Base 2 to 5) demonstrate preferred embodiments that also provide conditioning benefits.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oxidative hair dye composition comprising at least one oxidative dye and at least one oxidising agent in separate components, a first component and a second component, said first component comprising (a) a polyalkyleneglycol(n)alkylamine of the formula (I):

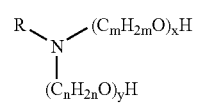

(I)

wherein each R is independently a saturated, unsaturated, straight or branched alkyl group having from 1 to about 30 carbon atoms, each m is 2 or 3, each n is 2 or 3, each x and each y are independently a number of 1 or more wherein the sum of each x and each y is from about 2 to about 9; and wherein the melting point of the polyalkyleneglycol(n)alkylamine is less than about 55° C.;

(b) at least one solid fatty compound; and
(c) water;

wherein said polyalkyleneglycol(n)alkylamine and said solid fatty compound together form a lamellar matrix; and wherein the viscosity of said first and said second component is independently from greater than about 1.5 Pas to about 20 Pas.

2. The oxidative hair dye composition according to claim 1, further comprising at least one organic acid having at least one acidic group, its salt, or mixtures thereof.

3. The oxidative hair dye composition according to claim 2, wherein said organic acid has from 4 to 22 carbon atoms.

4. The oxidative hair dye composition according to claim 2, wherein said organic acid is selected from oleic acid, linolenic acid, linoleic acid or mixtures thereof.

5. The oxidative hair dye composition according to claim 1, wherein R is an unsaturated or a saturated alkyl group having from about 8 to about 22 carbon atoms, m is 2 and the sum of x and y is from 2 to 7.

6. The oxidative hair dye composition according to claim 1, wherein said solid fatty compound comprises an alkyl chain having from about 16 to about 22 carbons.

7. The oxidative hair dye composition according to claim 2 comprising by weight from about 0.001% to about 4% of said oxidative dye or mixtures thereof and
(a) from about 0.1% to about 10% of a polyalkylene(n) alkylamine of the formula:

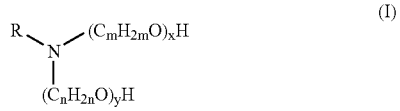
(I)

wherein R is a saturated, unsaturated, straight or branched alkyl group having from 1 to about 30 carbon atoms, m is 2 or 3, n is 2 or 3, x and y are independently a number of 1 or more wherein the sum of x and y is from about 2 to about 9, and wherein the melting point of the polyalkylene(n)alkylamine is less than about 55° C.;
(b) from about 0.1% to about 10% of said organic acid having at least one acidic group, its salt, or mixtures thereof, at the level such that the mole ratio of acidic groups from the organic acids to amine groups from polyalkyleneglycol(n)alkylamines is from about 1:5 to about 5:1;
(c) from about 0.1% to about 20% of said solid fatty compound; and
(d) water.

8. The oxidative hair dye composition according to claim 1, wherein said first and said second components are mixed prior to application to the hair and wherein the resultant mixture has a viscosity of from greater than 1.0 Pas to 20 Pas.

9. The oxidative hair dye composition according to claim 1, wherein said first component has a pH of from about 2 to about 13.

10. The oxidative hair dye composition according to claim 1, wherein said first or said second component or both further comprises at least one conditioning agent.

11. The oxidative hair dye composition according to claim 1, wherein said first or said second component or both further comprises a surfactant.

12. A method of dyeing human or animal hair comprising the steps of applying to the hair an oxidative hair dyeing composition according to claim 1 and subsequently rinsing said composition off the hair.

13. A method of dyeing and conditioning human or animal hair according to claim 12, comprising the steps of:
(1) first applying an oxidative dyeing composition to the hair and subsequently rinsing said composition from the hair; and then
(2) second applying a conditioning composition to the hair.

14. An oxidative hair dye composition comprising at least one oxidative dye and at least one oxidising agent in separate components, a first component and a second component, said first component comprising a viscosity forming matrix comprising:
(a) from about 0.25% to about 3% of a polyalkylene(n) alkylamine selected from the group consisting of PEG-2 soyamine, PEG-3 cocamine, PEG-5 cocamine, and mixtures therof;
(b) from about 0.1% to about 10% of at least one organic acid having at least one acidic group, its salt, or mixtures thereof, at a level such that the mole ratio of acidic groups from the organic acids to amine groups from polyalkyleneglycol(n)alkylamines is from about 1:5 to about 5:1;
(c) from about 1% to about 10% of at least one solid fatty compound, wherein said solid fatty compound is a substantially saturated fatty alcohol having from 16 to 22 carbon atoms and wherein said solid fatty compound is substantially a mixture of stearyl and cetyl fatty alcohol; and
(d) water; and
wherein the viscosity of said first and said second component is independently from about 2 Pas to about 5 Pas and wherein the resultant mixture has a viscosity of from about 2 Pas to about 5 Pas.

* * * * *